United States Patent [19]
Pennington

[11] Patent Number: 5,806,096
[45] Date of Patent: Sep. 15, 1998

[54] MEDICAL-TUBE RETAINING GARMENT

[76] Inventor: Jacqueline R. Pennington, 2314 S. 5th St., Ironton, Ohio 45638

[21] Appl. No.: 840,128

[22] Filed: Apr. 11, 1997

Related U.S. Application Data

[60] Provisional application No. 60/015,640 Apr. 19, 1996.
[51] Int. Cl.⁶ .............................. A41D 13/00; A41D 11/00
[52] U.S. Cl. ............................... 2/80; 2/83; 2/102; 2/111; 2/114; 604/179; 604/345
[58] Field of Search .................................... 2/80, 83, 102, 2/111, 114, 78.2, 78.3, 78.4, 108, 109, 69, 69.5, 401, 402, 408, 338, 48, 52; 604/345, 174, 179; 128/DIG. 26

[56] References Cited

U.S. PATENT DOCUMENTS

| | | | |
|---|---|---|---|
| 2,051,685 | 8/1936 | Dickson | 2/111 |
| 2,433,915 | 1/1948 | Long . | |
| 2,511,977 | 6/1950 | Garrison | 2/83 |
| 2,556,931 | 6/1951 | Miller | 2/114 |
| 2,666,203 | 1/1954 | Berman | 2/111 |
| 2,671,220 | 3/1954 | Geissmann | 2/80 |
| 2,704,070 | 3/1955 | Rudisill . | |
| 3,803,640 | 4/1974 | Ericson | 2/114 |
| 4,666,432 | 5/1987 | McNeish et al. | 604/174 |
| 4,688,270 | 8/1987 | Denicola et al. | 2/102 |
| 4,718,124 | 1/1988 | Sawicki et al. | 2/114 |
| 4,769,855 | 9/1988 | Tsai | 2/114 |
| 4,853,977 | 8/1989 | Foreman | 2/114 |
| 5,033,121 | 7/1991 | Larsen | 2/229 |
| 5,048,122 | 9/1991 | Prieur | 2/69 |
| 5,274,851 | 1/1994 | Simpkins, Sr. et al. | 2/108 |
| 5,398,340 | 3/1995 | Kibbee | 2/102 |
| 5,418,978 | 5/1995 | Hochman | 2/69 |

FOREIGN PATENT DOCUMENTS

| | | |
|---|---|---|
| 1027511 | 5/1953 | France . |
| 1193503 | 11/1959 | France .................................... 2/111 |
| 184460 | 6/1923 | United Kingdom . |

*Primary Examiner*—Amy B. Vanatta
*Attorney, Agent, or Firm*—Richard C. Litman

[57] ABSTRACT

A medical tube-retaining garment to deter patients, especially children, from disturbing a surgical wound site on the torso. An inner garment resembling a shirt or undergarment having a split back is affixed to an outer garment made of a wrappable, elastic bandage material. Both the outer and inner garments close over the back by overlapping portions having hook and loop type fasteners, which rear entry design deters the patient or child from detaching the garments. A crotch strap passes from front to back of the outer garment to deter the child from pulling up on the inner garment to reveal the surgery site. Similarly, shoulder straps of the inner garment deter the child from pulling the inner garment down to reveal the site. Secondary hook and eye fasteners prevent separation of the hook and loop fasteners. When the inner and outer garments are secured over the back the child is sufficiently deterred from gaining access to the implanted tubes.

12 Claims, 3 Drawing Sheets

MEDICAL-TUBE RETAINING GARMENT

CROSS-REFERENCE TO RELATED APPLICATION

This application claims the benefit of U.S. Provisional patent application Ser. No. 60/015,640, filed Apr. 19, 1996.

BACKGROUND OF THE INVENTION

1. Field of the Invention

The present invention relates generally to garments and more specifically to garments especially designed to retain surgically implanted medical tubes and the like.

2. Description of the Prior Art

In the medical arena, it is often beneficial for patients to have catheters or drainage tubes implanted into their bodies. Such implants sometimes remain in place for extended periods of time. The implants permit many patients to be treated on an outpatient basis; the drainage tubes allow impurities or harmful body fluids to escape and the catheters enable the administration of therapeutic agents without the painful insertion of needles into the vein. Additionally, many medical procedures can be accomplished at the patient's home through the use of the implant, thereby eliminating the necessity of frequent office visits.

Such implants, though advantageous to the patient and doctor, can also create risk for a patient not fully cognizant of its presence or reason for presence. The implants, many of which pass through the abdominal wall, normally inserted under the skin and into a large vessel such as a vein or urinary channel, are ordinarily held fast to the patient by tape and require surgical stitches of the surrounding area, any of which can cause irritation to the patient. In attempting to relieve the pain and irritation associated with implants, patients sometimes accidentally dislodge the inserts, particularly while sleeping or drowsy. The risk of dislodging implants is even greater in small children due to their lack of cognisance and natural tendency to touch and pull on items within their reach. When children are fitted with an implant, they tend to dislodge or even extract the implants, either through play, curiosity or an attempt to relieve pain and irritation.

The dislodging or extracting of medical implants can result in extreme medical emergencies, leading to emergency surgery or worse. Although an adult patient can understand the serious consequences of extracting the tube, in many instances children lack the mental aptitude to fully comprehend the potential for danger. There is, therefore, a need for a garment that will deter patients, especially children, from extracting or dislodging medical implants, the garment otherwise having the appearance of a normal garment. The present invention provides such a device.

Medical garments have been described in the patent literature. For example, U.S. Pat. Nos. 4,666,432 issued to McNeish et al. on May 19, 1987, U.S. Pat. No. 4,688,270 issued to Denicola et al. on Aug. 25, 1987, U.S. Pat. No. 5,048,122 issued to Prieur on Sep. 17, 1991, and U.S. Pat. No. 5,418,978 issued to Hockman on May 30, 1995, all describe medical garments, but each fail to disclose medical tube-retaining garments designed and configured to resemble normal undergarments while incorporating medical bandages. Furthermore, all of the above cited patents fail to disclose medical tube-retaining garments having closures that fasten the garment in the back, thus deterring access to the closure by the patient. Such feature would offer a particularly desirable advantage when the patient is a small child.

U.S. Pat. Nos. 2,433,915 issued to Long on Jun. 12, 1945, U.S. Pat. No. 2,704,070 issued to Rudisill on Jun. 19, 1953, U.S. Pat. No. 4,718,124 issued to Sawicki et al. on Jan. 12, 1988, U.S. Pat. No. 5,033,121 issued to Larsen on Jul. 23, 1991, French Brevet D'Invention No. 1,027,511 published on May 12, 1953, and United Kingdom Pat. Specification published on Jun. 28, 1923, all describe features of encircling garments, but fail to disclose medical garments which close in the rear of the garment and restrain medical implants.

None of the above inventions and patents, taken either singly or in combination, is seen to describe the instant invention as claimed.

SUMMARY OF THE INVENTION

The invention relates to a medical tube-retaining garment that deters patients, especially children, from disturbing a surgical wound site, particularly removing surgically implanted tubes passing out of the patient. An inner garment, resembling a shirt or undergarment and worn over the patient's body trunk next to the skin to comfortably cover the surgical site, is attached to an outer garment formed of a elastic bandage of sufficient length when stretched to wrap around the inner garment, thereby securing the inner garment over the trunk of the patient and the medical implant area. The outer and inner garments each have an open back fastenable by closures in the back, which helps deter a patient from easily reaching fasteners securing the garments and unreasonably removing the implant. Both the outer garment and inner garment are fastened by hook and loop type fasteners, which allow quick and easy attachment and detachment of the garments by others.

Additional securing means are provided to further deter tampering with the garments and the underlying surgical site. A crotch strap, passing from the front to the back portion of the outer garment and between the legs of the wearer, deters the wearer from pulling up on either inner or outer garments to reveal the surgical site. Similarly, the inner garment includes a shoulder strap, defining each arm hole of the inner garment, which deters the child from pulling the garment down to reveal the implanted tubes. Moreover, a supplemental locking closure, such as a hook and eyelet, is provided at the back portion of the outer garment to deter separation of the hook and loop fasteners by the wearer. When the lower and upper garments are secured by the fasteners and supplemental closure, the wearer is sufficiently deterred from gaining access to the implanted tubes.

Accordingly, it is a principal object of the invention to provide a garment that deters patients from disturbing a surgical wound site.

It is a further object of the invention to provide a medical tube-retaining garment having a inner garment for wearing over the torso of a patient and comfortably covering medical implants.

Still another object of the invention is to provide a medical tube-retaining garment wherein an outer garment elastically secures the inner garment over the medical implants and restricts removal and movement of both the inner garment and the medical implants.

It is another object of the invention to provide a medical tube-retaining garment having a crotch strap and shoulder straps which restrict pulling up the outer garment and pulling down the inner garment.

It is again an object of the invention to provide a medical tube-retaining garment that fastens at the back to make unfastening of the outer garment by the patient more difficult.

It is an object of the invention to provide improved elements and arrangements thereof in an apparatus for the purposes described which is inexpensive, dependable and fully effective in accomplishing its intended purposes.

These and other objects of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENT

Figure 1:
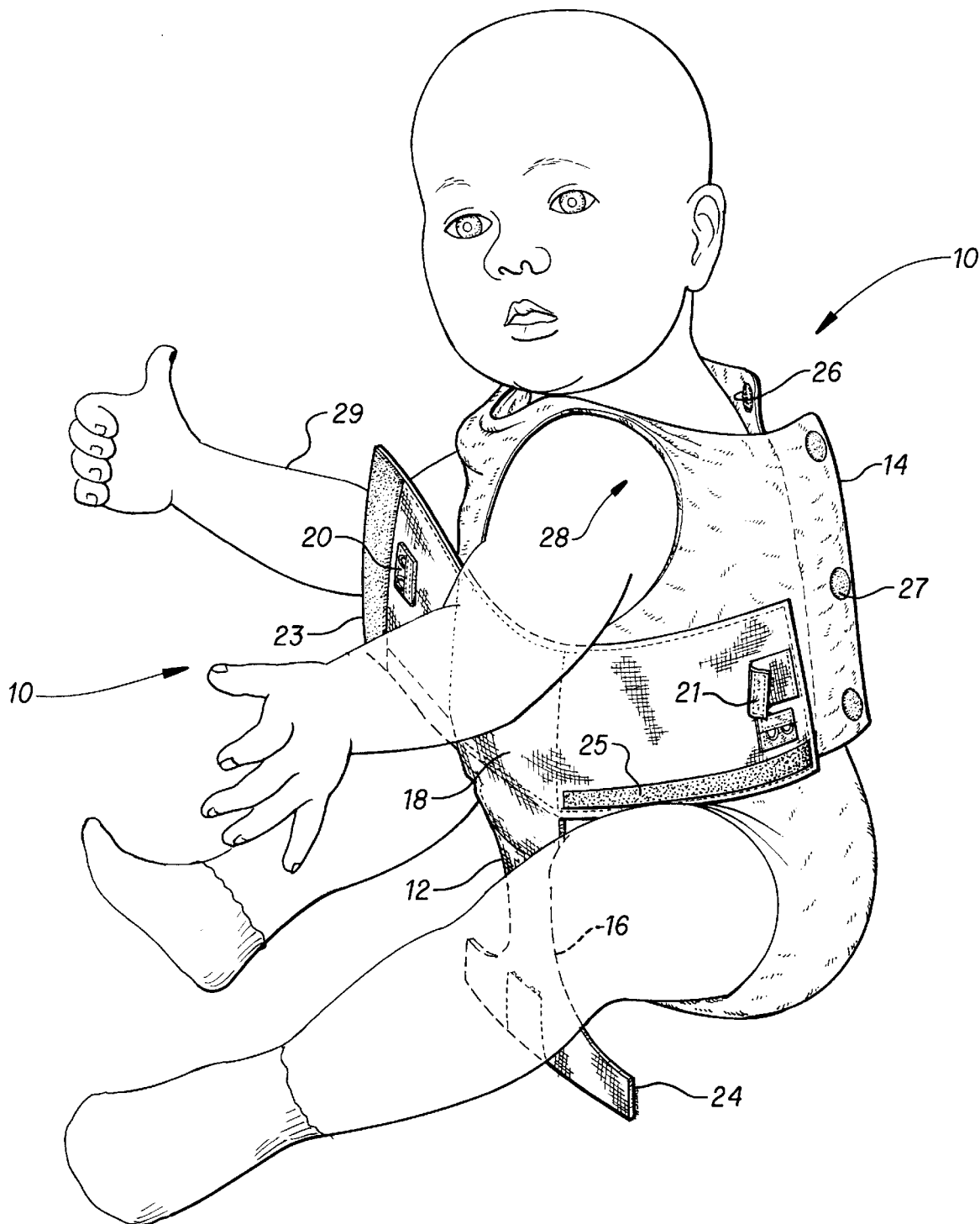
FIG. 1 is an environmental, perspective view of the present invention, showing the same in a partially closed configuration so as to more clearly reveal how the garment attaches to the child.
Figure 2:
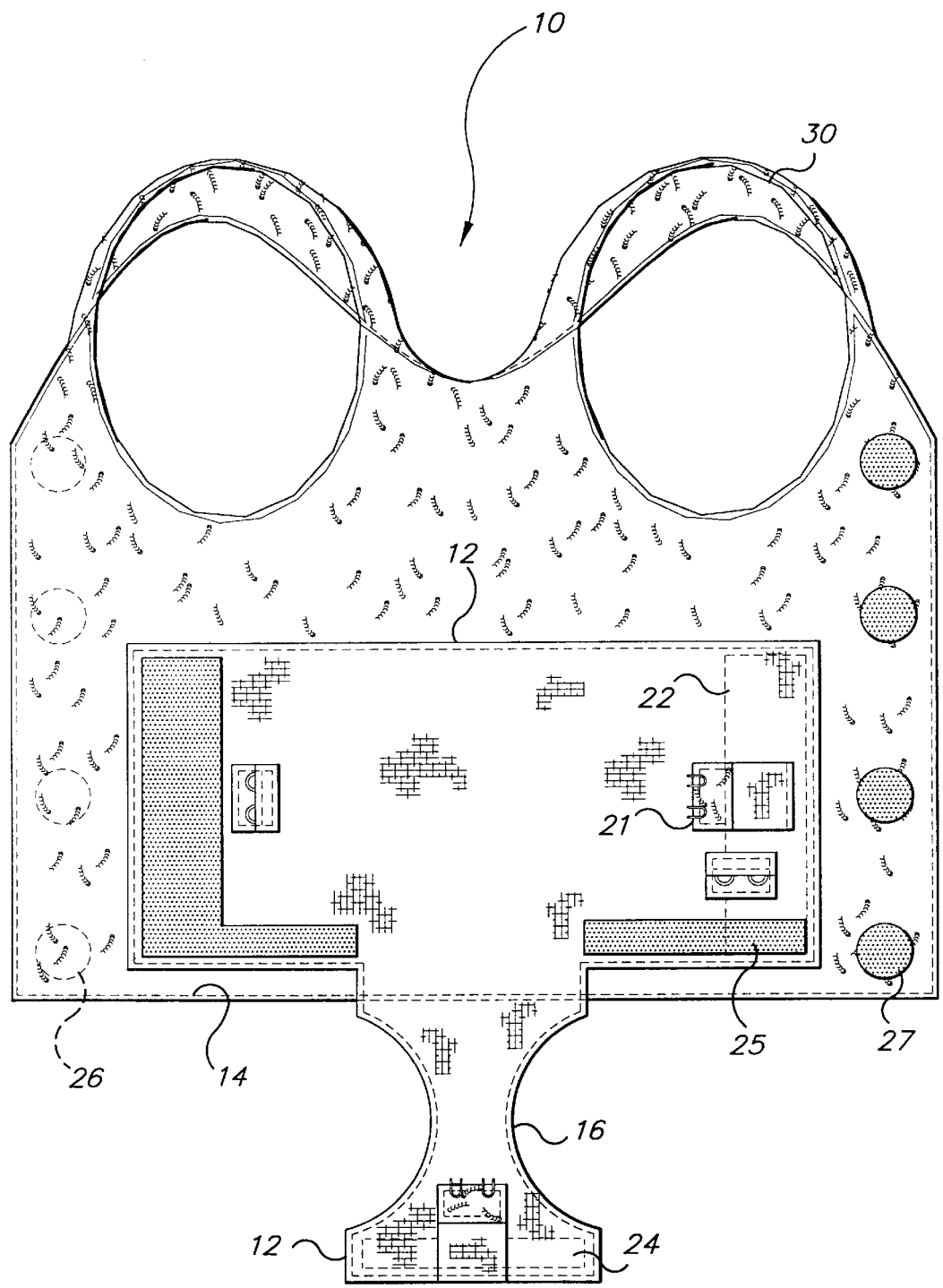
FIG. 2 is a front elevational view of the present invention in a flattened, fully open configuration.
Figure 3:
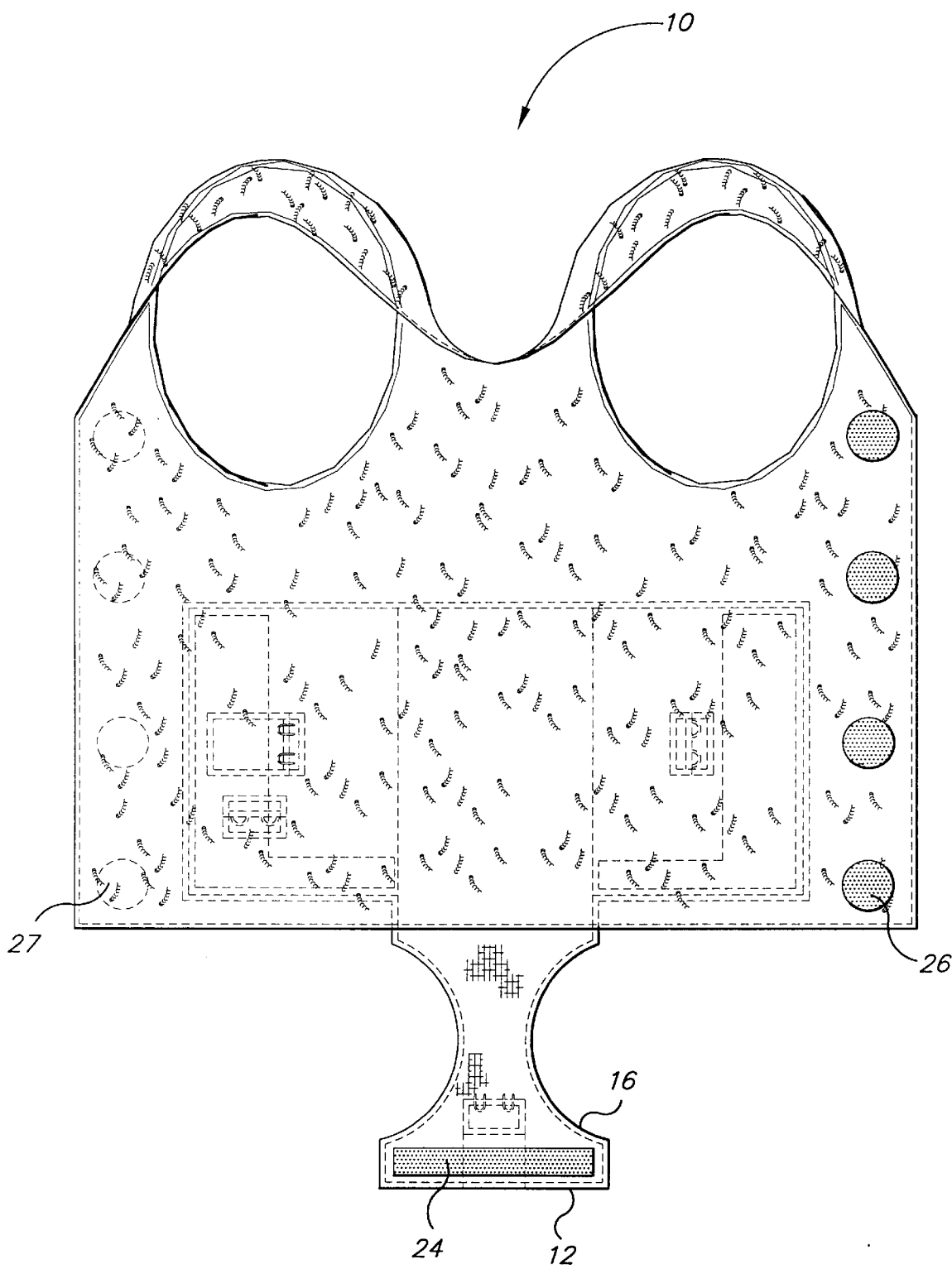
FIG. 3 is a rear elevational view of the present invention, also in a flat, fully open configuration.

In FIG. 1 of the drawings, the preferred embodiment of a medical garment 10 is shown dimensioned and configured to fit an infant. Medical garment 10 is depicted with inner garment 14 and outer garment 12 worn in a partially open condition by an infant. Inner garment 14 is attached to outer garment 12 such that medical garment 10 is a one-piece garment. In contrast, FIG. 2 depicts medical garment 10 shown from the front of the garment 10, whereas FIG. 3 shows medical garment 10 viewed from the rear of the garment, each view showing a flattened, laid-out position of the garment 10.

Referring now to the Figures together and turning first to the features of inner garment 14, the inner garment 14 is functionally designed to resemble a normal shirt or undergarment, intended to comfortably and absorbently protect the skin and surgical wounds of the infant. The fabric material of the inner garment is preferably a hypo-allergenic fabric, such as cotton, which is both comfortable to the touch and absorbent; the material should also breathe (so that the incision will not "sweat") thereby decreasing the likelihood of infection. Arm openings 28 are defined in the inner garment to receive the arms 29 of the patient from the front; the arm openings may form shoulder straps which support the inner and outer garments over the trunk of the infant. However, a sleeved embodiment can also be easily envisioned. The inner garment has an open, split back which fastens to close in the back, in the nature of a traditional medical gown, which feature enables the advantage of avoiding raising or bending backwards of the patient's arms. The rear closure thus reduces the risk of discomfort or disturbing a wound site by limiting the necessary motion of a patient to don the garment 10.

Inner garment 14 is provided with complementary fasteners to close the open back behind the patient, including a first attachment 26 opposingly positioned to a complementary second attachment 27. In the preferred embodiment, first and second attachments 26,27 are complementary hook and loop type fasteners, although any easily and quickly attachable or detachable fasteners would be appropriate for use. In use and as more fully described below, the inner garment is first placed on and next to the skin of the patient and fastened in the back before proceeding with closure of the outer garment, which fully secures the whole garment over the wound site.

Focusing next on the structure of outer garment 12, the preferred material for outer garment 12 comprises a wrappable compression bandage made of a stretchable, elastic fabric, as normally used in applications for joints and other extremities to keep down swelling. Such compression bandages are commonly referred to in the art as "Ace" bandages. The outer garment 12 is dimensioned in length and configured to band the infant around the trunk of the infant. As can be appreciated from the Figures, front section 18 of outer garment 12 overlays inner garment 14 in the areas of the abdomen and lower chest of the patient, and is affixed to the inner garment 12 at the front section 18, leaving two free end portions 50,51. Outer garment 12 is attached to inner garment 14 by means of stitching or any other appropriate means. Free end portions 50,51 stretch to overlap one another and are provided with complementary fasteners, inner attachment 23 and outer attachment 22, to secure the overlapping free end portions 50,51 together. A crotch strap 16 is affixed to front section 18 and is configured to pass between the patient's legs. Crotch strap 16 removably attaches via a crotch strap fastener, in the preferred embodiment comprising attachment 24 which removably joins to a complementary lower attachment 25 and the lower part of inner attachment 23, each affixed to the outer garment L2.

As best appreciated from FIG. 2, the inner attachment 23 is affixed to free end portion So of the outer garment 12 to allow fastening to the mating outer attachment 22 attached to the free end portion 51. When the stretchable material is wrapped and secured about the trunk of the infant, attachments 22,23,24,25 are each brought into overlapping alignment with one another, fastening the free end portions 50,51 and crotch strap 16 in a stretched condition. Inner attachment 23, lower attachment 25, outer attachment 22 (shown in FIG. 2) and crotch strap attachment 24 are each preferably complementary parts of a hook and loop type fastener, although any fasteners that can be easily and quickly attached or detached would be appropriate.

Crotch strap 16 prevents outer garment 12 from riding up and exposing the surgical site, and, minimizes the patient's ability to intentionally expose the implant site by pulling up on inner garment 14 or outer garment 12. Having slipped the inner garment 14 over the trunk of the infant (to cover, for example, an abdominal drainage tube which, although not shown, can be easily and effectively run from the implant site out and under the medical garment 10), the inner attachment 23, the lower attachment 25, the outer attachment 22 and crotch strap attachment 24 are thus brought together to secure the outer garment 12 over the inner garment 14 closely and firmly to the skin of the patient. By so securing the outer garment 12, the compression bandage is tightly stretched around the inner garment 14 and the infant, which secures and stabilizes exiting abdominal tubes, preventing significant movement thereof, and thus deterring the patient from dislodging or extracting any tubes.

As previously noted, the garment 10 features an open back and fasteners which allow both the inner and outer garments 14,12, to be closed over the back of the infant or patient, directly opposite front section 18. This feature provides not only the advantage of easily clothing the patient, but also deters removal of the garment by limiting the patient's ability to successfully reach the attachments 22,23,24,25 and detach outer garment 12. Moreover, to add extra security and deter patients who might try to reach around and detach attachments 22,23,24,25, two-part, complementary safety attachments 20,21 and 30,31 provide an added level of tamper resistance,.although the attachments may be optionally added. The preferred embodiment of the safety attachments 20,21 and 30,31 are complementary hook and eye assemblies, the hooks 33 being attached to an elastic and flexible band 34, and the eyes 36 each affixed to the outer garment 10 wrapping the infant. When the outer garment is closed, each eye 36 is complementarily positioned to receive a hook 33 when the band 34 is brought over and spans the first attachments 26 and the juncture of the split back of the outer garment 12. The eyes 36 are further positioned so that the band 34 must be slightly stretched to engage the hook 33 in the eye 36, so that a firm tension exists between the hook and eye to prevent inadvertent disengagement when the band 34 is released.

As can be observed from FIG. 2, the safety attachments 20,21 are positioned at opposing ends of the outer garment 12 for securing the wrap of the cuter garment around the trunk of the patient, and the safety attachments 30,31 are attached to the crotch strap 16 and back of the outer garment for securing the crotch strap 16 behind the patient. Once secured, attachments 20,21 and 30, 31 are sufficiently difficult to uncouple to deter a patient from doing so.

Using the medical garment 10, an infant is best dressed by laying the medical garment 10 flat on a surface as shown in FIG. 3 (rear facing up) and placing the infant on his/her stomach on top of the medical garment 10. After the arms are passed through the openings 28, second attachment 27 is then brought over the back of the child (not shown). First attachment 26 is then brought over and mated with second attachment 27, thus securing the inner garment 14. Outer garment 12 is then secured over inner garment 14, inner attachment 23 being folded over and mating with outer attachment 22. Crotch strap 16 is then passed up over the crotch area of the child, placing the end of crotch strap 16 on the lower back, mating attachment 24 with the lower attachment 25. By so securing the garment 10 to the infant, crotch strap 16 prevents medical garment 10 from riding up, and shoulder straps 30 deter the child from pulling medical garment down, thus minimizing risk of exposure of the surgical site. Since crotch strap 16 folds up towards the lower back, there are no attachments in the front and, in turn, no attachments easily reachable by the child. This advantage greatly adds to the difficulty facing any child trying to detach medical garment 10. Moreover, only the crotch strap 16 need be unfastened to remove diapers worn by the patient infant. The final level of protection is applied by fastening safety attachments 20,21 and 30,31. At this point medical garment 10 is firmly secured around the body of the child, minimizing the danger of accidentally extracting or moving inserted tubes or otherwise disturbing the surgical site.

It is to be understood that the present invention is not limited to the sole embodiment described above, but encompasses any and all embodiments within the scope of the following claims.

I claim:

1. A medical tube-retaining garment for use by a human wearer comprising:

an inner garment for wearing over the upper trunk of the wearer, said inner garment defining a pair of arm openings, a front and a split back, said inner garment having a plurality of complementary fastening means for closing said split back together and thereby securing said inner garment around the upper trunk of the wearer; and, an outer garment comprising:

an elastic band dimensioned and configured to wrap around the upper trunk of the wearer, said band affixed to said front of said inner garment, said band having a free first end portion for wrapping around the trunk of the wearer and a free second end portion extending in an opposing direction from said free first end portion and dimensioned in length to permit overlap over said split back of said inner garment and said first free end when said outer garment is closed; and complementary attachment means including an inner attachment affixed to said first end portion and an outer attachment affixed to said second end portion, each for matingly fastening said outer garment closely around the wearer;

whereby, when said inner garment is worn in contact with a surgical wound site of the wearer and upon closing said split back with said complementary fastening means, said first end portion and said second end portion of said elastic band of said outer garment is passed over a closed split back and tightly fastened by said complementary attachment means to form an encircling tensioned bard, thereby closely securing said inner garment to the trunk of the wearer and restricting disturbance of said wound site.

2. The medical tube-retaining garment according to claim 1, wherein said inner garment is made of a breathable fabric soft to the touch.

3. The medical tube-retaining garment according to claim 1, wherein said inner garment is made of cotton.

4. The medical tube-retaining garment according to claim 1, wherein said complementary attachment means and said complementary fastening means are a hook and loop type fastener.

5. The medical tube-retaining garment according to claim 1, further comprising a crotch strap dimensioned and configured to pass over the crotch and between the legs of the wearer, said crotch strap attached proximate to said front and having a free terminal portion for overlapping said outer garment proximate said split back, and further comprising securing means for attaching said free terminal portion to said outer garment proximate said split back.

6. The medical tube-retaining garment according to claim 5, wherein said securing means is a hook and loop type fastener.

7. The medical tube-retaining garment according to claim 5, further having a safety attachment for preventing said securing means of said crotch strap from separating when closed.

8. The medical tube-retaining garment according to claim 7, wherein said safety attachment is a complementary hook and eye assembly, said hook affixed to an elastic strap attached to one of either said crotch strap or said outer garment and dimensioned in length to overlap onto the other of said crotch strap or said outer garment, said eye being attached to said other of said crotch strap or said outer garment and positioned to receive said hook when said elastic strap is tensioned.

9. The medical tube-retaining garment according to claim 1, further having a safety attachment for securing said complementary attachment means of said outer garment from separating when closed.

10. The medical tube-retaining garment according to claim 9, wherein said safety attachment is a complementary hook and eye assembly, said hook affixed to an elastic strap attached to one of either said free first end portion or said free second end portion and dimensioned in length to overlap onto the other of said free first end portion or said free second end portion, said eye being attached to said other of said free first end portion or said free second end portion and positioned to receive said hook when said elastic strap is tensioned.

11. The medical tube-retaining garment according to claim 1, wherein said outer garment is made of a woven elastic fabric having a resilient memory.

12. The medical tube-retaining garment according to claim 11, wherein said fabric is a compression bandage.

* * * * *